(12) United States Patent
Barbic et al.

(10) Patent No.: US 7,892,427 B2
(45) Date of Patent: Feb. 22, 2011

(54) APPARATUS AND METHOD FOR MAGNETIC-BASED MANIPULATION OF MICROSCOPIC PARTICLES

(75) Inventors: Mladen Barbic, South Pasadena, CA (US); Jack J. Mock, Cardiff By The Sea, CA (US); Andrew P. Gray, San Marcos, CA (US)

(73) Assignee: California Institute of Technology, Pasadena, CA (US)

( * ) Notice: Subject to any disclaimer, the term of this patent is extended or adjusted under 35 U.S.C. 154(b) by 58 days.

(21) Appl. No.: 12/229,975

(22) Filed: Aug. 28, 2008

(65) Prior Publication Data

US 2009/0092509 A1    Apr. 9, 2009

Related U.S. Application Data

(62) Division of application No. 10/411,771, filed on Apr. 11, 2003, now abandoned.

(60) Provisional application No. 60/372,322, filed on Apr. 12, 2002.

(51) Int. Cl.
B01D 35/06 (2006.01)
(52) U.S. Cl. .................. 210/222; 209/29; 209/213; 209/214; 210/94; 210/695
(58) Field of Classification Search .............. None
See application file for complete search history.

(56) References Cited

U.S. PATENT DOCUMENTS

| | | | |
|---|---|---|---|
| 5,670,712 A | 9/1997 | Cleveland et al. | |
| 5,925,818 A | 7/1999 | Cleveland et al. | |
| 6,172,902 B1 * | 1/2001 | Wegrowe et al. | 365/158 |
| 6,400,549 B1 | 6/2002 | Davis et al. | |
| 6,828,786 B2 | 12/2004 | Scherer et al. | |
| 2002/0009759 A1 * | 1/2002 | Terstappen et al. | 435/7.23 |
| 2003/0158474 A1 | 8/2003 | Scherer et al. | |
| 2004/0021073 A1 | 2/2004 | Barbic et al. | |
| 2006/0181097 A1 | 8/2006 | Choi et al. | |

OTHER PUBLICATIONS

Ahn et al., "A Planar Variable Reluctance Magnetic Micromotor with Fully Integrated Stator and Coils", J. of Microelectromechanical Systems, vol. 2, No. 4, pp. 165-172 (Dec. 1993).

(Continued)

Primary Examiner—Krishnan S Menon
Assistant Examiner—Dirk Bass
(74) Attorney, Agent, or Firm—Greer, Burns & Crain Ltd.

(57) ABSTRACT

Apparatus and method for manipulating particles on a micro- or nano-scale. An embodiment of the present invention includes a magnetic micro-manipulation technique that utilizes micro-coils and soft magnetic microscopic wires for localized manipulation of particles. Another embodiment of the present invention uses magneto-static interaction between two magnetic microscopic wires to mechanically manipulate particles. Yet another embodiment of the present invention combines a magnetic particle with a magnetic manipulator or other device for generating magnetic fields to operate as a micro-fluidic micro-motor. Other embodiments of the present invention employ a magnetic separation system employing porous membranes partially filled with magnetic wires.

20 Claims, 14 Drawing Sheets

OTHER PUBLICATIONS

Barbic et al., "Electromagnetic micromotor for microfluidics applications", Applied Physics Letters, vol. 79, No. 9, pp. 1399-1401 (Aug. 2001).

Barbic, "Magnetic wires in MEMS and bio-medical applications", Journal of Magnetism and Magnetic Materials 249, pp. 357-367 (2002).

Caraffini et al., "Magnetically Actuated Metallic MicroGripper", SPIE Conference on Microbiotics and Micromanipulation, SPIE vol. 3519, Nov. 1998.

Joung et al., "Micropumps Based on Alternating High-Gradient Magnetic Fields", IEEE Transactions on Magnetics, vol. 36, No. 4, pp. 2012-2014 (Jul. 2000).

Mandjour et al., "High-sensitivity broadband microwave spectroscopy with small nonresonant coils", Rev. Sci. Instrum. 57, pp. 1100-1106 (Jun. 1986).

O'Barr et al., "Preparation and quantitative magnetic studies of single-domain nickel cylinders", J. Appl. Phys. 79, pp. 5303-5305 (Apr. 1996).

Olson et al., "High-Resolution Microcoil 1H-NMR for Mass-Limited, Nanoliter-Volume Samples", Science, vol. 270, pp. 1967-1970 (Dec. 1995).

Quake et al., "From Micro- to Nanofabrication with Soft Materials", Science, vol. 290, pp. 1536-1540 (2000).

Rogers et al., "Using microcontact printing to fabricate microcoils on capillaries for high resolution proton nuclear magnetic resonance on nanoliter volumes", Appl. Phys. Lett. 70, pp. 2464-2466 (1997).

Rugar et al., "Magnetic force microscopy: General principles and application to longitudinal recording media", J. Appl. Phys. 68, pp. 1169-1183 (Aug. 1990).

Sanny et al., "Microwave electron spin resonance spectrometer with operation to 54 mK in a dilution refrigerator", Rev. Sci. Instrum. 52, pp. 539-541 (Apr. 1981).

Sidles et al., "Magnetic Resonance Force Microscopy", Rev. Mod Phys. 67, pp. 249-268 (Jan. 1995).

Todorovic et al., "Miniature high-sensitive quartz tuning fork alternating gradient magnetometry", Appl. Phys. Lett., vol. 73, No. 24, pp. 3595-3597 (Dec. 1998).

Unger et al., "Monolithic Microfabricated Valves and Pumps by Multilayer Soft Lithography", Science, vol. 288, pp. 113-116, 2000.

* cited by examiner

APPARATUS AND METHOD FOR MAGNETIC-BASED MANIPULATION OF MICROSCOPIC PARTICLES

PRIORITY CLAIM

This application is a division of U.S. application Ser. No. 10/411,771, filed Apr. 11, 2003, now abandoned incorporated by reference herein, which claims priority of Provisional Patent Application Ser. No. 60/372,322, filed Apr. 12, 2002, under 35 U.S.C. §119.

STATEMENT OF GOVERNMENT INTEREST

The present invention was made with Government assistance under National Science Foundation Grant No. NSF-DMR 97-24535, National Institute of Health Grant No. PHSH601959-02, and ONR (DARPA) Grant No. N00014-00-1-0632. The Government has certain rights in this invention.

FIELD OF THE INVENTION

The present invention relates generally to micro-scale and nano-scale devices and systems. The present invention additionally relates to micro-electromechanical systems (MEMS). Another field of the invention is micro- and nano-scale particle manipulation, e.g., handling of chemical and biological materials in analysis systems.

BACKGROUND OF THE INVENTION

Micromanipulation and characterization of objects ranging in size from atomic to micrometer dimensions has become one of the central features of modern science. Optical trapping methods are known for manipulating latex micron-sized balls attached to objects of biological interest at room temperature. In addition, systems based on carbon nanotubes have been utilized for physical tweezing of micro-objects.

Miniaturizing mechanical, optical, magnetic, and electronic components is part of a major effort in development and use of micro- and nano-scale devices and systems. For example, there has been a significant amount of micro-electromechanical systems (MEMS) research with the goal of reducing the size of systems into sub-millimeter dimensions.

As part of the development and operation of these miniaturized systems, it is highly desired to provide methods and systems for manipulating very small (micro- or nano-scale, for example) particles in various environments, including air, vacuum, or fluid.

As an example, there exists a specific interest in the manipulation of magnetic objects. Magnetic tweezers have found wide uses in biological applications, such as in the investigations of the physical properties of the cytoplasm, mechanical properties of cell surfaces, and elasticity and transport of single DNA molecules. For cell studies, most of these techniques rely on the micromanipulation of a magnetic particle positioned inside a cell wall or bound on the surface of a cell, while the single molecule investigations involve linking the magnetic particle on one end of the molecule strand. In all of these studies, micromanipulation is performed with a device consisting of permanent or soft coil-wound magnets with macroscopic dimensions. Typical forces available through these techniques are in the range of 0.1-10 pN.

SUMMARY OF THE INVENTION

Several applications that exploit the properties of magnetic wires and micro-coils are provided by the present invention. One type of embodiment includes a magnetic manipulation apparatus that utilizes a micro-coil wound around a soft magnetic wire for positioning of particles. Another embodiment of the present invention provides an apparatus for mechanical manipulation of a particle using magneto-static interaction between two magnetic micro-wires affected by a magnetic actuator, which supplies either a local or external magnetic field. Still other embodiments of the present invention combine a rotor including a microscopic particle with a stator including a plurality of magnetic manipulators for generating magnetic fields to operate as a micro-scale motor. Other embodiments of the present invention employ a magnetic separation system for microscopic particles including a membrane having a plurality of pores where one or more of the pores contains a magnetic wire.

DETAILED DESCRIPTION OF THE INVENTION

Figure 1:
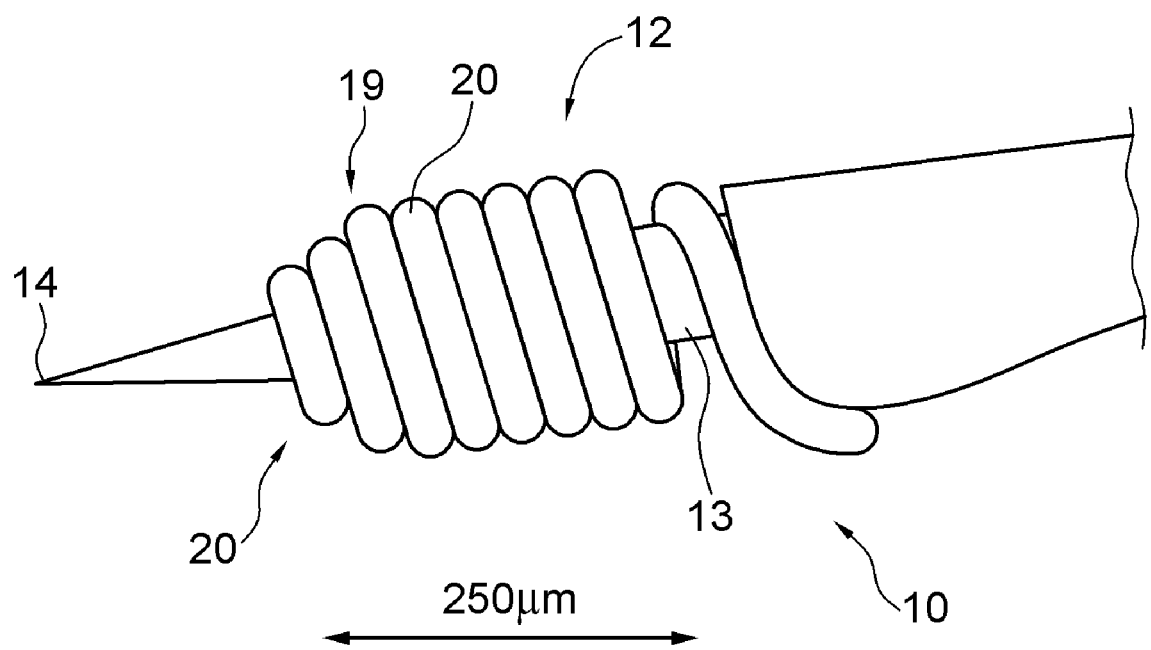
FIG. 1 is a photograph of a magnetic manipulator according to an embodiment of the present invention.

As the principles and tools used in conventional micro- and nano-fabrication of devices and systems stem from the semiconductor industry, electrostatic principles dominate conventional actuation tasks, and magnetic components are generally avoided due to added expense and lack of processing know-how. However, there are potential advantages to using magnetic components in micromachines if fabrication and cost challenges can be overcome. Magnetic components can generally create larger forces at a larger distance than their electrostatic counterparts. Additionally, since the magnetic materials are responsive to the magnetic fields and field gradients generated by the current carrying wires, they tend to be of low input impedance, rather than being high impedance voltage devices, as is the case for electrostatic actuators.

The present invention provides several methods and systems for magnetic manipulation of particles in various environments. In addition to basic manipulation such as moving, positioning, arranging, etc. of discrete particles by magnetic and magnetic/mechanical methods, the present invention provides methods incorporating particle manipulation into more complex systems. Devices and methods provided by the invention can potentially provide micro-scale, cost-effective techniques to manipulate particles. Applications include, but are not limited to, the fields of engineering, including but not limited to micro-electromechanical systems (MEMS), and biology.

Certain preferred embodiments of the present invention provide magnetic or magneto-mechanical operation of microscopic tweezers or clamps using magnetic principles. A magnetic manipulator is disclosed according to particular preferred embodiments of the present invention that allows manipulation of microscopic particles (e.g. micro- or nano-scale particles) in various environments. A preferred magnetic micro-manipulation system and method utilizes a magnetic manipulator having micro-coils and magnetic microscopic wires working together for localized positioning of micron-sized magnetic objects. This preferred instrument provides a non-invasive, low-cost alternative to the optical trapping techniques conventionally used in biological micro-manipulation, for example. This magnetic manipulator also has potential for applications directed to studies of mechanical properties of some basic molecular systems.

Other preferred embodiments of the present invention use a magnetic manipulator or other magnetic field generator in combination with soft magnetic microscopic wires to form a system for mechanically manipulating particles. Magnetic microscopic wires offer several features that make them attractive for use in a number of applications. Since elongated magnetic microscopic wires with a diameter of 1 μm or less are generally fully magnetized (single domain) along the long axis due to their small size and elongated shape, they are by default permanent magnets, and require no energy to be magnetized by outside sources. Their small size also translates into large gradient magnetic fields that these magnetic microscopic wires generate, and therefore large magnetic forces that they can apply. The source of these strong gradient fields can be at the ends of the wires, or along the entire wire if a magnetic field is used to magnetize the wire perpendicular to the wire long axis. Furthermore, the synthesis of magnetic micro-wires has become very cost effective. This makes magnetic micro-wires potentially disposable, a particularly attractive feature for massively parallel MEMS and biomedical systems where considerations of cost are of importance. Additionally, the fact that the microscopic wires of this size are permanently magnetized allows for both attractive and repulsive forces to be magnetized. Based on these principles, several embodiments of magnetic microscopic wire applications are contemplated by the present invention.

Preferred embodiments of the invention use a magnetic microscopic wire as a source of a large gradient magnetic field for the development of micro-magneto-mechanical systems (MMMS) such as nano-magnetic tweezers and ultra-high gradient magnetic separation applications. Current micro-scale tweezers are generally electrostatic in nature. However, magnetic forces are generally stronger than their electrostatic counterparts, and therefore it can be advantageous to use magnetic components. Also, electrostatic devices are generally high impedance, voltage driven devices, while magnetic devices are generally low impedance.

According to a preferred embodiment of the present invention, the forces between arms of microscopic wires are magnetic in nature, and the operation of the tweezers, i.e. opening and closing of the tweezers, is based on the basic properties of the small magnetic wires. Preferably, the single domain state property of a small magnetic wire is used for applying attractive forces between the arms of the tweezers (the nano-wires). By applying appropriate macroscopic or local magnetic fields (by the magnetic manipulator, for example) the tweezers can be opened and closed as desired.

The microscopic wires may be prepared by electrodeposition. In certain embodiments, multi-component microscopic wires having magnetic and non-magnetic parts are contemplated. In this way, more complex objects can be constructed that allow cylindrical structures, including non-magnetic structures, to be joined together by magnetic forces. This multi-functionality may be useful in, for example, biological and engineering applications.

Other preferred embodiments of the present invention use magnetic manipulators and/or magnetic microscopic wires in combination with other components to form additional devices or systems. An embodiment of the invention includes extending the microcoil/magnetic microscopic wire system into the development of an electric motor. This rotational motor can be manufactured relatively simply and inexpensively, and extends the use of magnetic microscopic wires in microfluidic "lab-on-a-chip" systems, for example. Inexpensive synthesis of magnetic microscopic wires makes them virtually disposable, a particularly attractive feature for micro-fluidics systems. An additional embodiment of the invention provides an ultra-high gradient magnetic separation apparatus.

Figure 2:
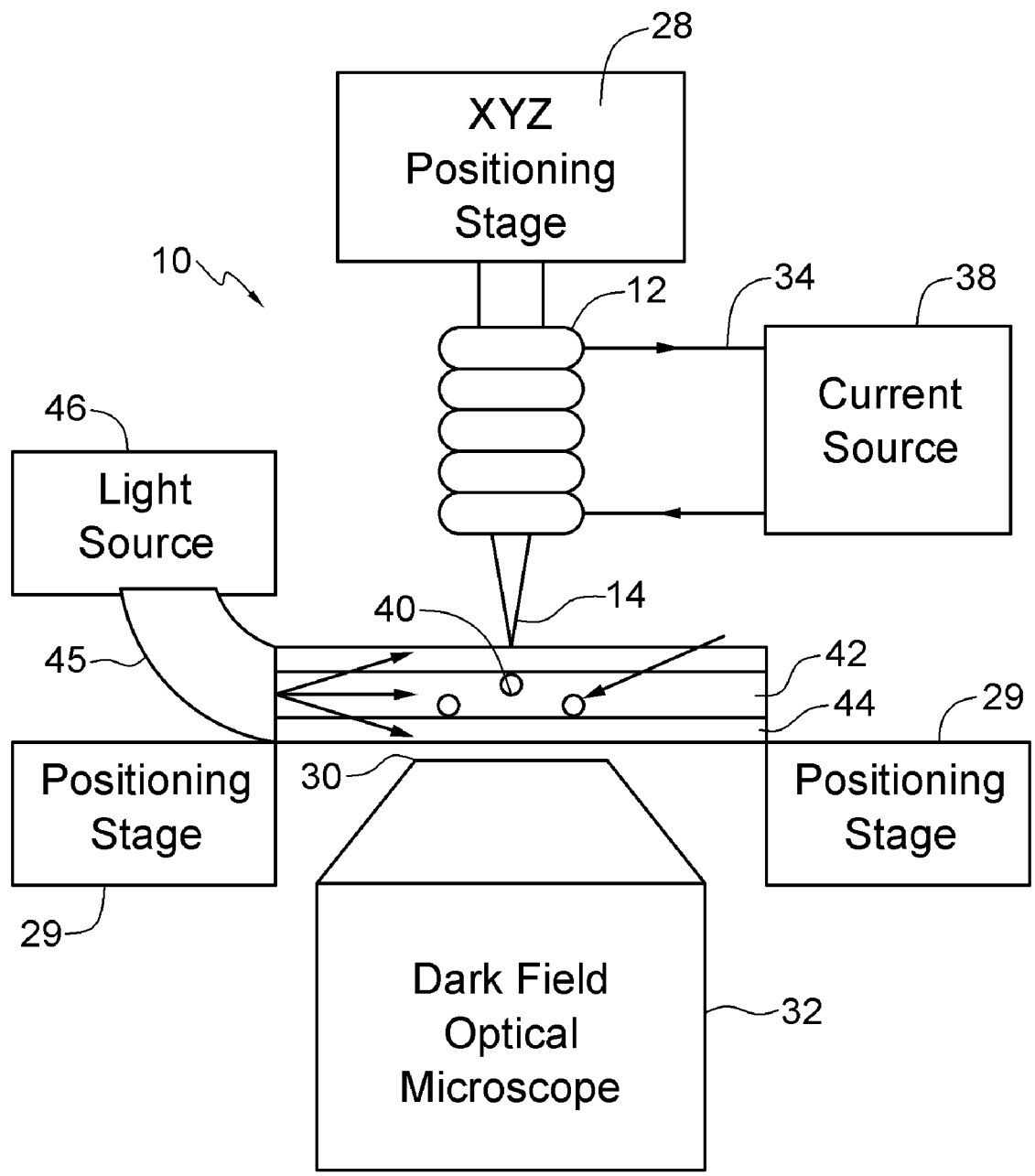
FIG. 2 is a schematic view of a magnetic manipulator positioned near particles for manipulation.

Referring now to the drawings, FIGS. 1 and 2 show a magnetic micromanipulator 10 according to an embodiment of the present invention that utilizes a helical, three-dimensional micro-coil 12 disposed about a generally cylindrical soft magnetic wire 13 terminating in a micro-tip 14 for localized positioning of micron-sized magnetic objects. The magnetic manipulator 10 shown by example in FIGS. 1 and 2 is preferably fabricated by winding the micro-coil 12, for example a small, e.g. 25 μm, diameter, copper magnet wire, around a small, e.g. 50 μm, diameter soft magnetic wire 13, as a nonlimiting example, a soft ferromagnetic wire, by a suitable method. The micro-coil is electrically isolated from the wire 13. A preferred winding design of the micro-coil 12 includes two radially inner and outer wound helical coil layers 18, 19 of insulated wire such as copper wire, though two layers are not required, with a number of turns 20 for each layer, preferably 6-8 turns, though the number of turns may vary. The magnetic wire 13 extends along a central axis, and the micro-coil 12 includes a helical axis substantially co-axial with the central axis of the magnetic wire. The wire of the layers 18, 19 may be insulated by suitable insulation, with a thickness of, for example, 1-5 μm, thereby permitting the micro-coil 12 to be wound closely around the wire 13.

To create high field gradients for the magnetic micro-tip 14, the soft magnetic wire 13 is etched into a sharp probe, for example 1-5 μm diameter at the end of the tip, and may be formed by, as a nonlimiting example, electrochemically etching in aqueous 40% sulfuric acid solution at 3V. The tip 14 is then positioned in the vicinity of the micro-coil 12, as shown in FIG. 1, preferably within an approximate distance of the length of one of the turns 20, to be maximally magnetized by the coil fields.

The micro-coils 12 and magnetic micro-tips 14 are preferred for producing magnetic forces in particle manipulation applications, since the forces on a magnetic bead depend on the field dependent magnetization of the bead, and the magnetic field gradient at the bead. Since the magnetic field from a coil such as the micro-coil 12 is inversely proportional to the coil diameter, and the field gradient from the magnetic tip 14 is inversely proportional to the tip dimensions, minimization of both of these parameters in the design of the magnetic micro-manipulator 10 is advantageous.

Figure 3:
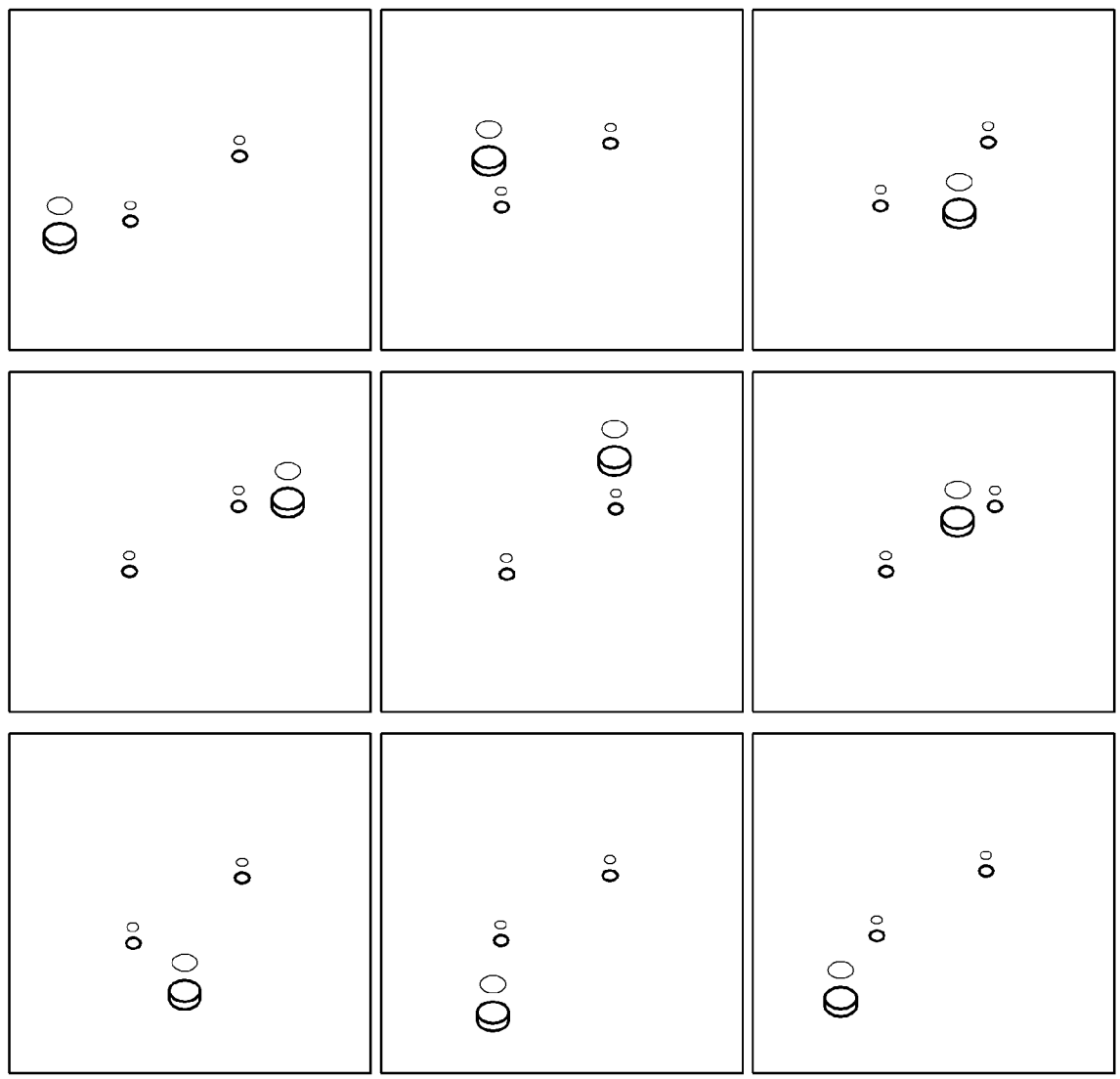
FIG. 3 is a sequence of images showing a particle being manipulated.

In an experimental setup using the magnetic manipulator 10 shown schematically in FIG. 2 the tip 14 of the magnetic manipulator 10 was placed on a mechanical stage 28 for positioning the tip above a viewing lens 30 of a dark field optical microscope 32. The manipulator 10 as shown includes suitable current delivery devices such as leads 34 coupling the coil 12 at ends of the insulated wire to a current source 38 such as a programmable constant current source for tunable operation of the device. The current source 38 preferably allows selective increasing or decreasing of the magnetic field and magnetic field gradients at the tip 14. Sample particles 40 to be manipulated within a fluid 42 were placed inside a rectangular cross section quartz capillary tube 44 with 40 μm capillary wall thickness. Light illumination was coupled to the capillary tube 44 from a 1 mm diameter optical fiber 45 connected to a white light source 46. The capillary tube 44 containing the magnetic particles 40 was placed between the tip 14 and the lens 30, movably positioned by stages 29 and the tip was positioned within several microns of the outside capillary tube surface. Because of the differences in the index of refraction of the capillary tube 44 and the surrounding air, light was confined to the capillary tube and did not illuminate the manipulator tip 14. Therefore, there is no spurious scattering from the tip 14 that would obscure the light scattered from the particles 40. This has the advantage of de-coupling the manipulation component of the experiment from the optical investigation of the samples. In order to demonstrate the manipulation of the samples 40 using the manipulator 10 and the scanning probe 28, 2.8 μm superparamagnetic beads were placed into the capillary tube 44 in the fluid 42, and 1 μm polystyrene beads were added into the same solution. After finding an area where there were two closely spaced non-magnetic beads, and using the manipulator 10 with 100 mA current through the micro-coil 12, all of the magnetic beads were removed to clear the area. A single one of the magnetic beads was selected to perform a second manipulation demonstration. FIG. 3 shows successive images of the magnetic bead manipulated so as to trace a "figure eight" around the non-magnetic beads. The non-magnetic polystyrene beads in FIG. 3 are 10 μm apart, and sub-micron positioning resolution can be achieved. The high dark background contrast in FIG. 3 is due to the illumination method used in the experimental micromanipulation technique. Although the tip 14 of the micromanipulator 10 is very close to the particle 40, there is no observable scattered light from the tip, due to the total internal reflection at the outside capillary surface. Forces of 10 pN and sub-micron positioning control were demonstrated on the 2.8 μm diameter superparamagnetic beads. Stronger forces on particles are possible by, for example, using the methods of pulsed currents through the micro-coil 12, winding additional coil turns, or using thinner capillary tube walls.

Preferably, the complete manipulator 10, including the micro-coils 12 and the soft magnetic wire 16 having the tip 14 (without the leads) exhibits a volume of less than 1 mm$^3$. This allows the manipulator 10 also to be used in various applications requiring magnetic manipulation where miniature size of the manipulator is preferred.

Other embodiments of the invention combine the magnetic manipulator 10 or other device for application of a magnetic field with magnetic wires to provide magneto-mechanical tweezers, which may be used in a number of applications. These embodiments are based in part on a principle of magneto-static attraction or repulsion between two permanent magnets. In preferred embodiments of the invention, the magnets are microscopic wires for example, having a diameter range of 10 nm-1 μm and made of any of various magnetic materials, that, due to their small size and elongated shape, have permanent magnetization (single domain) along their long axis. When two such wires are brought into proximity of each other, they are attracted to or repelled from one another depending on how their magnetizations are oriented.

Figure 4:
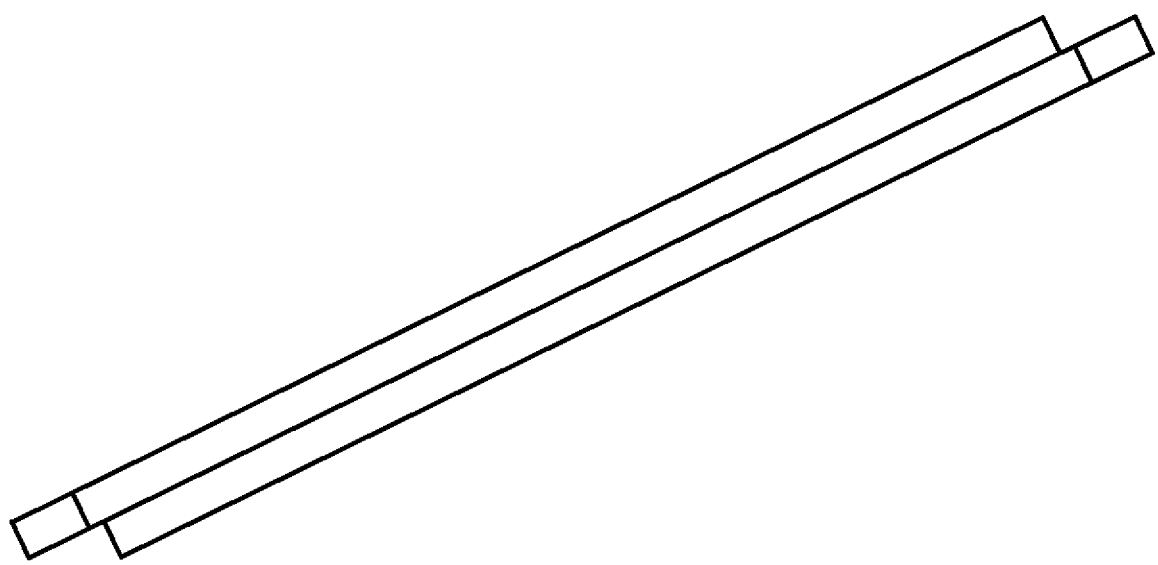
FIG. 4 is a photograph of a pair of magnetic microscopic wires joined to form magnetic mechanical tweezers according to another embodiment of the present invention.
Figure 5:
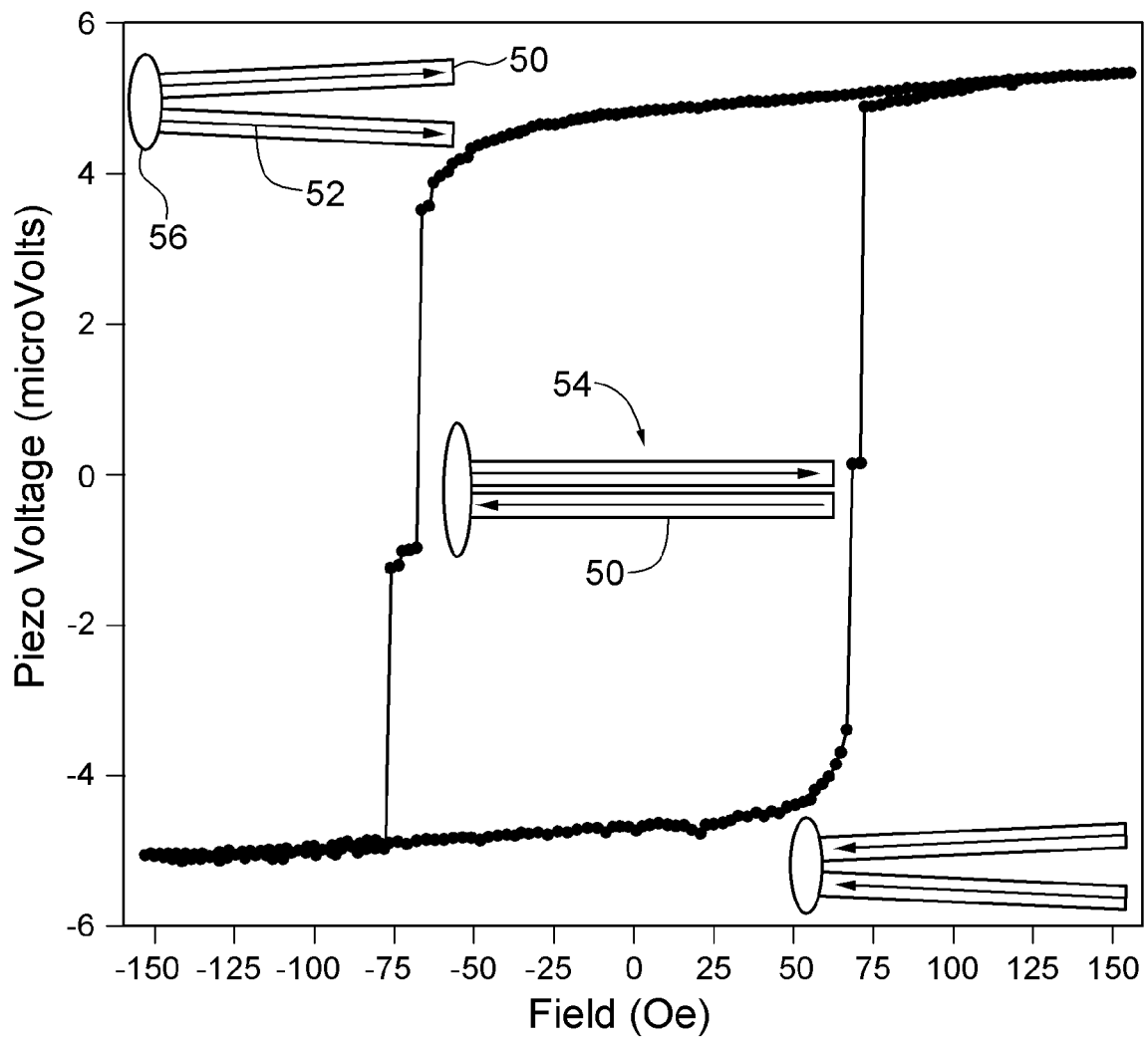
FIG. 5 is a measured hysteresis loop of a pair of magnetic microscopic wires demonstrating three stable magnetic configurations with inset schematic views of open and closed magnetic microscopic wires showing magnetization configurations of each wire.

FIGS. 4 and 5 show an optical figure and schematic diagram, respectively, of two, 40 μm long, 1 μm diameter, Ni magnetic microscopic wires 50 that are attracted to each other when magnetization vectors 52 (indicated by directional arrows) are antiparallel. When the magnetization vectors of the wires were made parallel to each other, the wires repelled. The microscopic wires 50 shown in FIG. 4 may be brought into contact with each other using the previously described magnetic micro-manipulator 10. The opposite poles of the microscopic wires 50 are attached to each other, and form a natural clamping system. Gold ends of the microscopic wires 50 shown in FIG. 4 are remnants of the plating cathode film from the electro-deposition process. This method of attractive or repulsive forces between the two microscopic wires 50 based on their relative magnetizations can be used as a magneto-mechanical clamp or tweezers system 54, as shown in FIGS. 4-7.

As one preferred method of opening and closing the tweezers 54, FIG. 5 shows a method where application of an external field by a magnetic actuator, such as the magnetic micro-manipulator 10, or electromagnet or permanent magnet to the tweezers is used to selectively orient the magnetization 52 of the two wires 50 parallel (as shown in the top and bottom inset figures) or antiparallel (as shown in the center inset figure) to each other. FIG. 5 also shows an example of a hysteresis loop by a high sensitivity magnetometer of two wires demonstrating tuning of magnetization of the two wires 50 to be parallel or antiparallel to each other by application of an external magnetic field. This measurement reveals clear regions of three stable configurations of this magneto-static system where the magnetizations 52 of the two wires 50 can be parallel or antiparallel with respect to one another. By placing a boundary condition, as a nonlimiting example, a flexible adhesive, on one side of each of the microscopic wires 50 so that, for example, the wires are fixed at one end and/or joined together at one end and are free to open and close at the other end, the tweezers 54 can be opened and closed in a manner similar to macroscale tweezers to mechanically secure and, by moving the tweezers, manipulate particles.

Figure 6A:
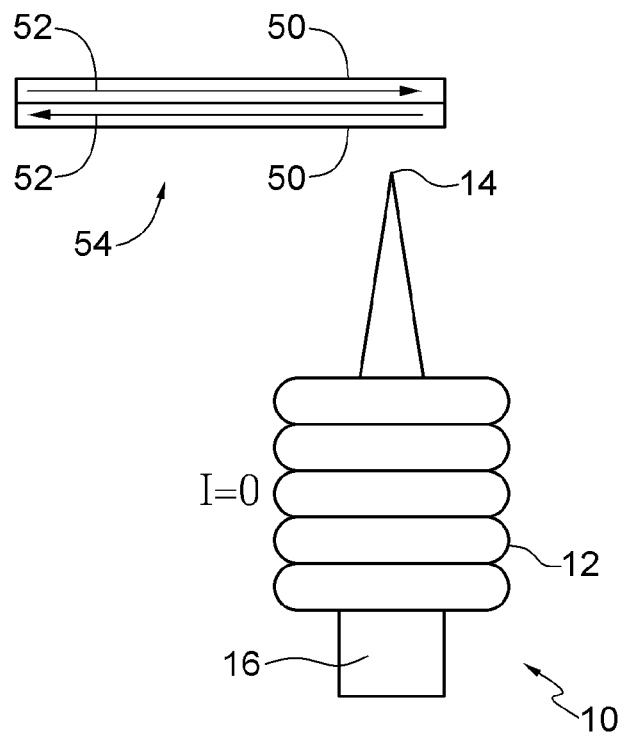
FIG. 6 is a schematic view of a pair of magnetic microscopic wires being closed and opened, respectively, by a magnetic manipulator.
Figure 6B:
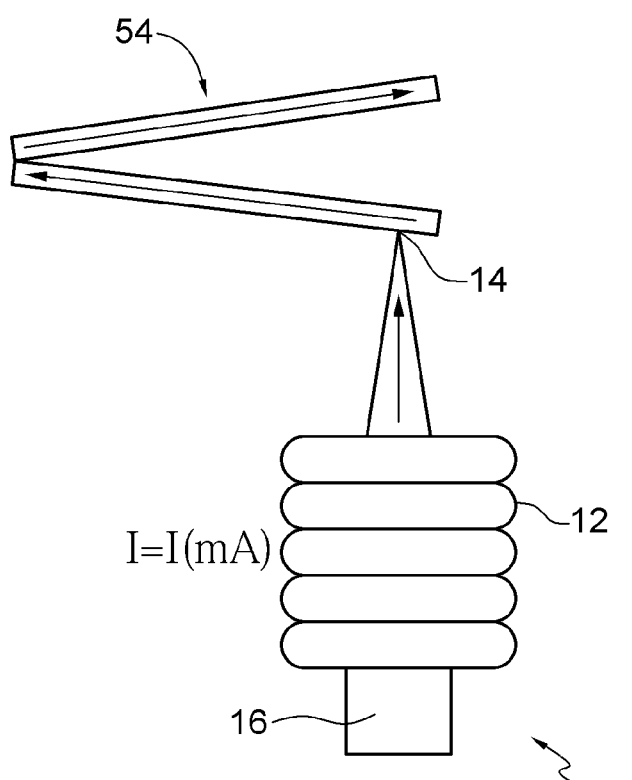
Figure 7:
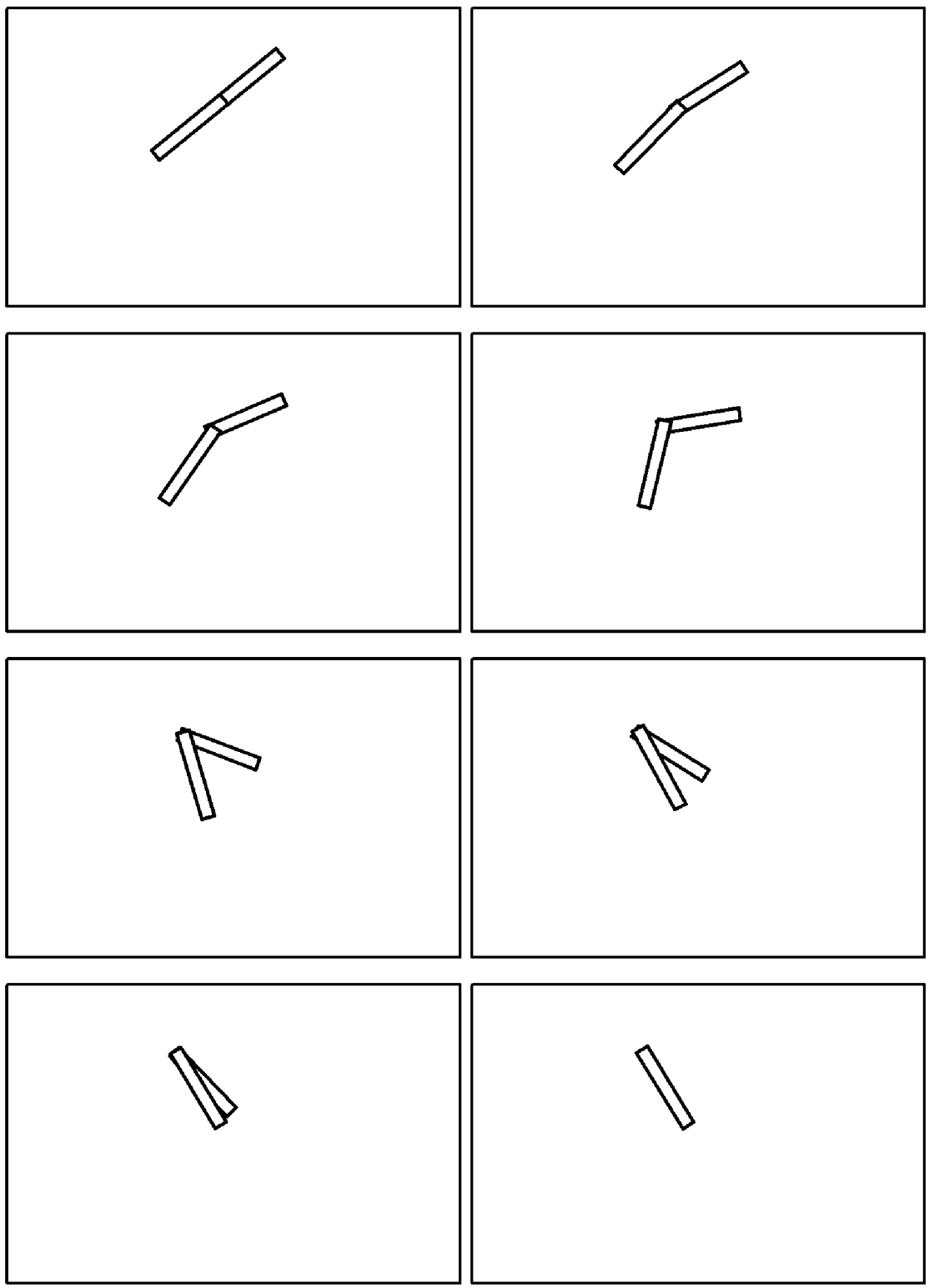
FIG. 7 is a sequence of photographs demonstrating controlled joining of a pair of magnetic microscopic wires.

FIG. 6 shows an alternative method of operating tweezers. By locally applying a field by a magnetic actuator such as the magnetic micro-manipulator 10 or other suitable device to ends of the microscopic wires (as shown in the diagram on the right), the pole of one wire is attracted to the manipulator while the pole of the other wire is repelled due to the opposite direction of the magnetizations. Thus, one of the microscopic wires 50 can be made attractive to the manipulator tip while the other is repulsed from the tip, resulting in separation of the tweezers arms if the force between the two tweezers arms is smaller than the force applied by the micro-manipulator, and allowing the tweezers to open. When the micro-manipulator 10 is not operating, as shown in the left diagram, the microscopic wires 50 of the tweezers 54 close. In other words, when the local field from the micro-manipulator 10 is removed, the tweezers' arms will be magnetically attracted to each other resulting in the closing of the tweezers system. FIG. 7 shows a sequence of images demonstrating controlled joining of two, 9 µm long, 0.25 µm diameter, electrodeposited Ni cylindrical wires. The micro-scale tweezers 54 can be used in, for example, engineering and biological applications where physical grabbing or squeezing of objects is required for transport, manipulation, or other purposes.

In addition to purely magnetic microscopic wires, alternative embodiments of the present invention provide manufacture of multi-component microscopic wire pairs 70 (FIG. 8C) by forming multi-component microscopic wires 72 (FIGS. 8A-8C) using sequential electro-deposition of different materials. Such multi-component microscopic wires 72 may include combinations of magnetic and non-magnetic metals in cylindrical shape along their length, so that the non-magnetic cylinders may be joined. One particular application of the multi-component microscopic wire pairs 70 is in the studies of biological systems, such as molecules that need to be examined by Raman spectroscopy using plasmon resonant enhancement between two silver microscopic wires, for example cylindrical wires. It has been predicted that the electromagnetic field enhancement is significantly increased when the two metal (preferably silver) cylindrical surfaces are within close proximity (on the order of Angstroms), to each other. For spectroscopy, the electromagnetic enhancement effect typically only applies to the silver nanowire 75 with diameters of 1-100 nm, for example. However, intentionally bringing two metallic cylinders together for such purposes has not been practically possible.

Figure 8A:
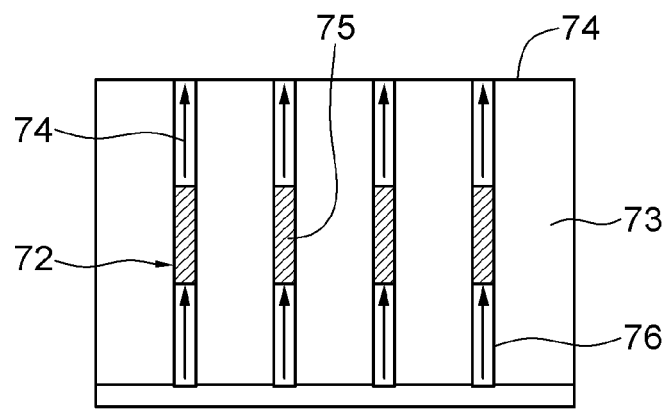
FIGS. 8A-8C are a schematic view of a sequence for joining multi-component microscopic wires.
Figure 8B:
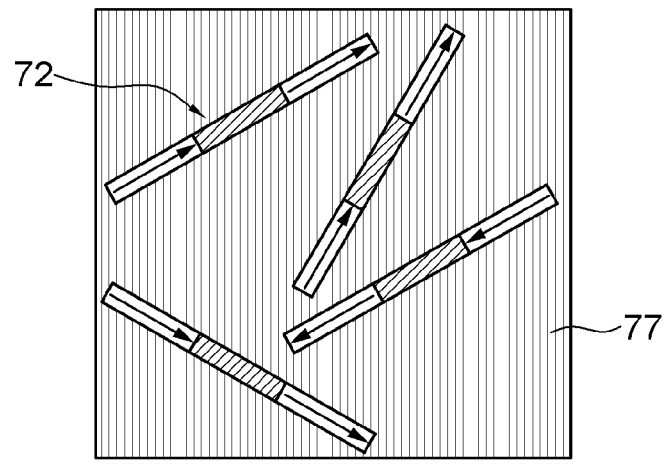
Figure 8C:
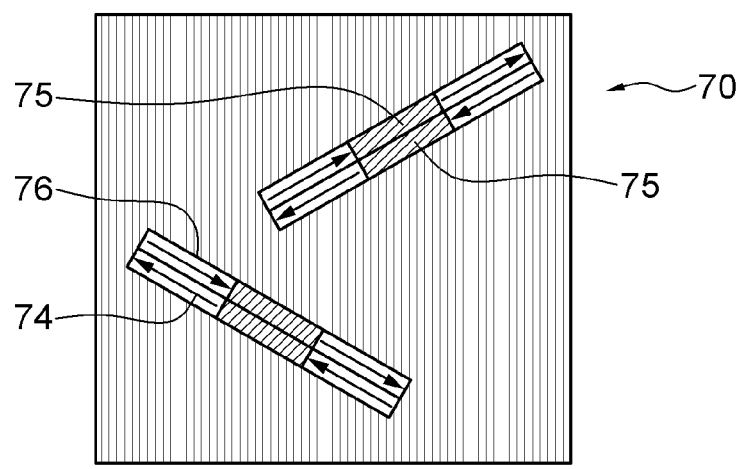

FIGS. 8A-8C show a method of accomplishing this task through producing a number of the multi-component microscopic wires 72, each having a preferably cylindrical cross-sectional shape, by sequential electrodeposition within a membrane 73 (FIG. 8A) of magnetic/nonmagnetic/magnetic sequences, for example nickel/silver/nickel metal microscopic wires 74, 75, 76, and then, removing, for example dissolving, the membrane to release the particles into a fluid 77 (FIG. 8B). Such multi-component microscopic wires 72 could then be brought into contact with each other (FIG. 8C) by application of an external magnetic field, such as by the magnetic manipulator 10, although it is likely pairs of multi-component wires 72 will self-assemble due to the long-range magneto-static interaction between the magnetic portions of the multi-component wires.

Figure 9:
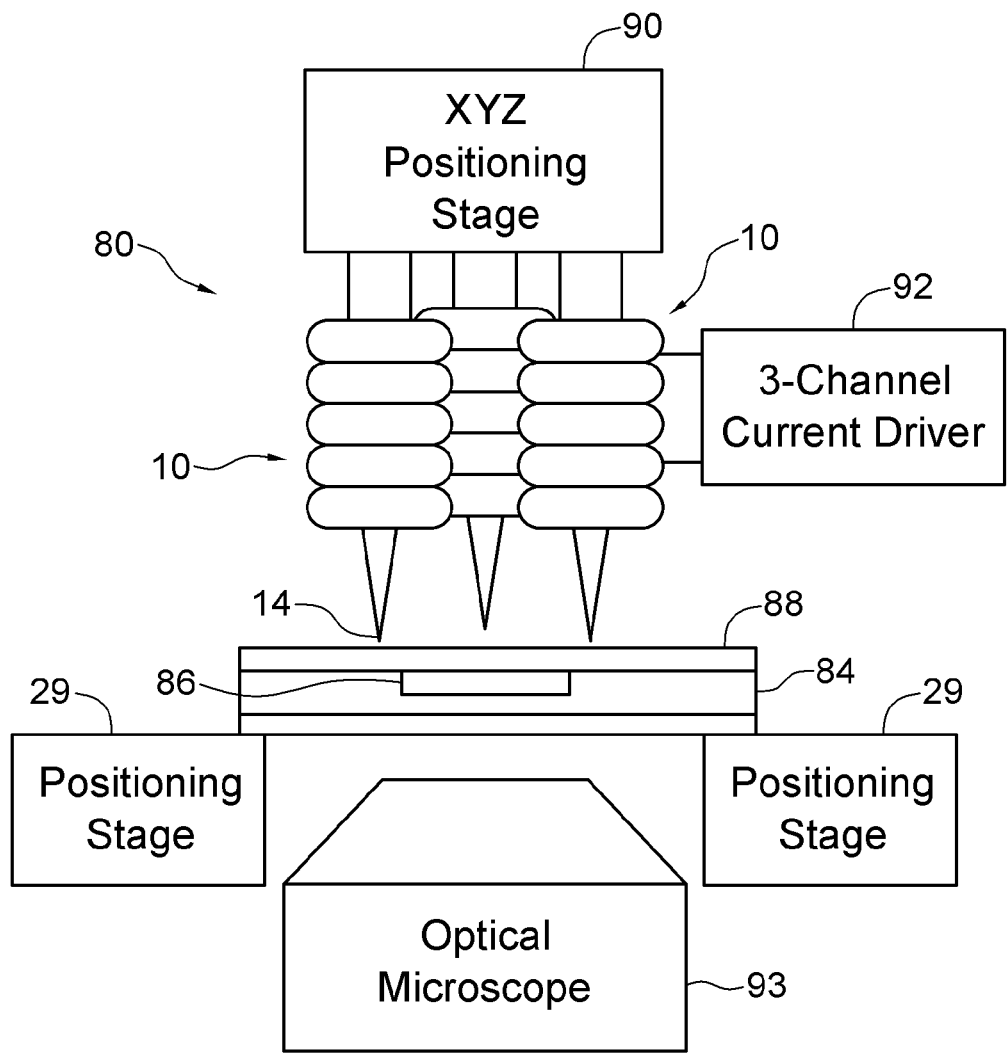
FIG. 9 is a schematic side view of a motor having a stator of magnetic manipulators and a micro-particle rotor according to another embodiment of the present invention.
Figure 10:
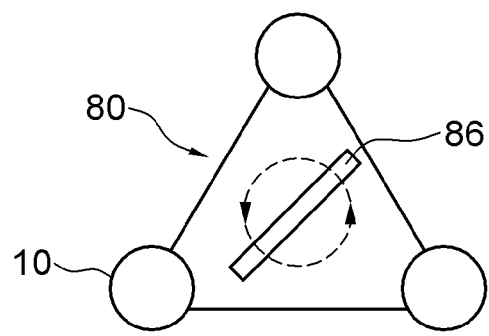
FIG. 10 is a schematic top view of a motor.
Figure 11:
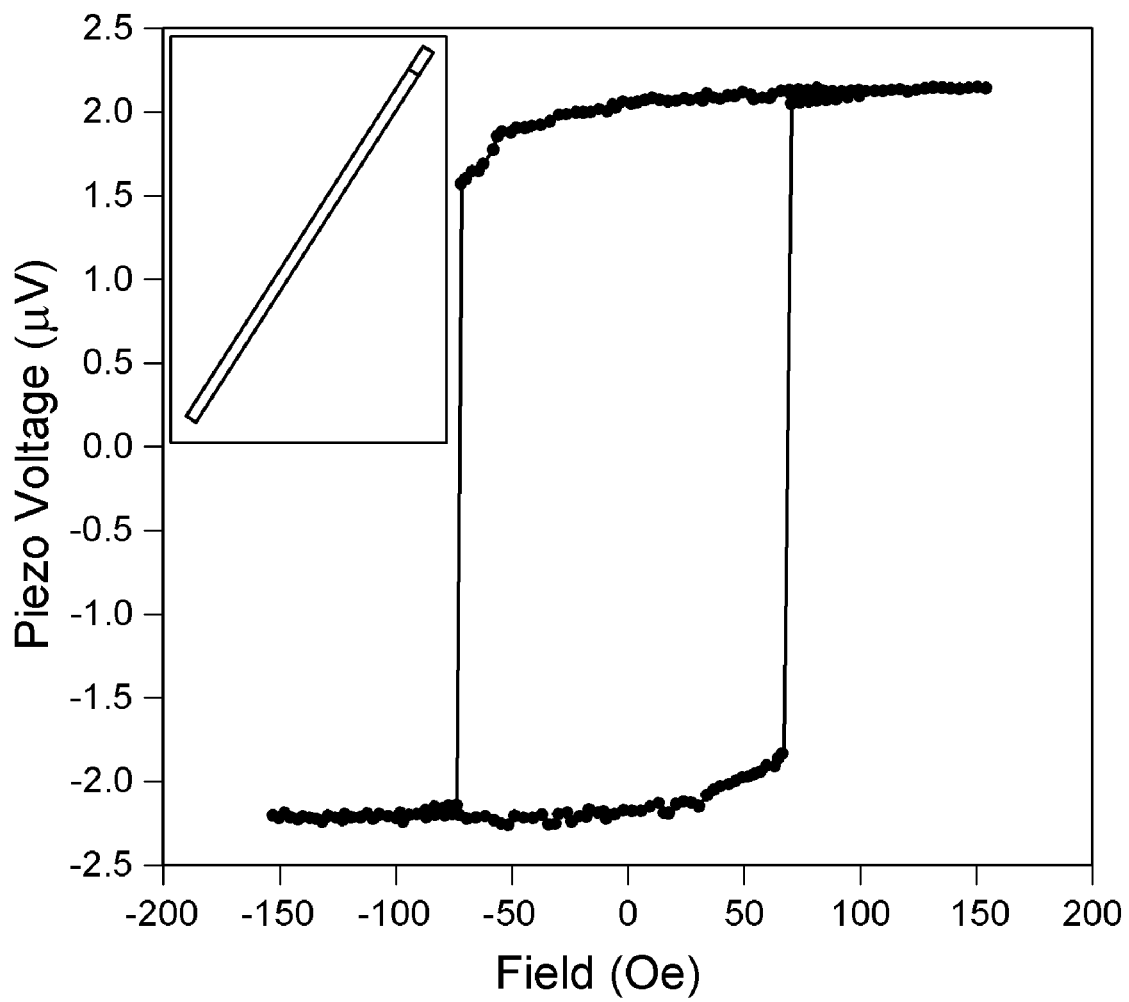
FIG. 11 shows a hysteresis loop of an individual single-domain micro-particle.

Manipulation of magnetic objects by the micro-manipulator 10 as described above can be extended to applying torques and forces on a magnetic single domain particle inside a fluid. For example, the micro-manipulator and single domain particle can act together as a micro-fluidic micro-motor 80, as shown in FIG. 9. Magnetic micro-motors with sub-millimeter dimensions have conventionally been fabricated by semiconductor processing techniques. An embodiment of the present invention miniaturizes and simplifies micro-motor 80 design by arranging a plurality (as shown, three) magnetic manipulators 10, with micro-manipulator coils 12 and tips 14, into a symmetrical (as shown, an equilateral triangle) arrangement, as shown in FIGS. 10-11, to form a multi-(as shown, three) phase stator 82. The three-phase stator 82 of the micro-motor 80 is brought into proximity (for example, within the size of the stator) of the single-domain particle 86, preferably but not necessarily positioned outside of a fluid 84, while the individual single-domain particle 86, such as the magnetic microscopic wire 54, placed in the fluid acts as the rotor. The single domain particle 86 of the rotor may be, for example, a cylindrical nickel particle, 40 µm long and 1 µm in diameter, fabricated by electro-deposition of nickel into a porous nanochannel membrane, such as a membrane similar to the membrane 73. After electrodeposition, the particle is released into the fluid 84, contained in a capillary tube 88 for example, by chemically etching the substrate (the membrane) in weak acetic acid. Fabrication of the columnar magnetic single domain particles 86 by electrodeposition into porous membranes is an attractive feature, since various porous membrane hosts are now available, including nano-channel glass array, anodized alumina, and polycarbonate membranes. The fact that the particle 86 is permanently magnetized also allows for both attractive and repulsive forces to be applied to the particle from the soft magnetic poles (the tips 14) of the stator 82. In order to confirm that these magnetic particles 86 were magnetically single domain, a square hysteresis loop of an individual particle was measured using ultra-high sensitivity magnetometry, sample results of which are shown FIG. 11.

Figure 12:
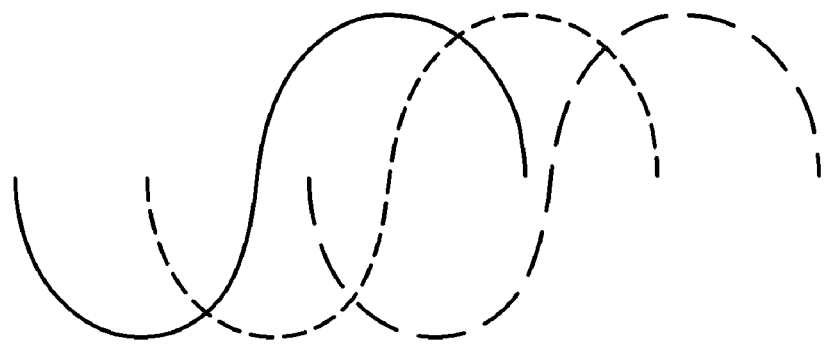
FIG. 12 is an illustration of currents applied to micro-coils of a stator.
Figure 13:
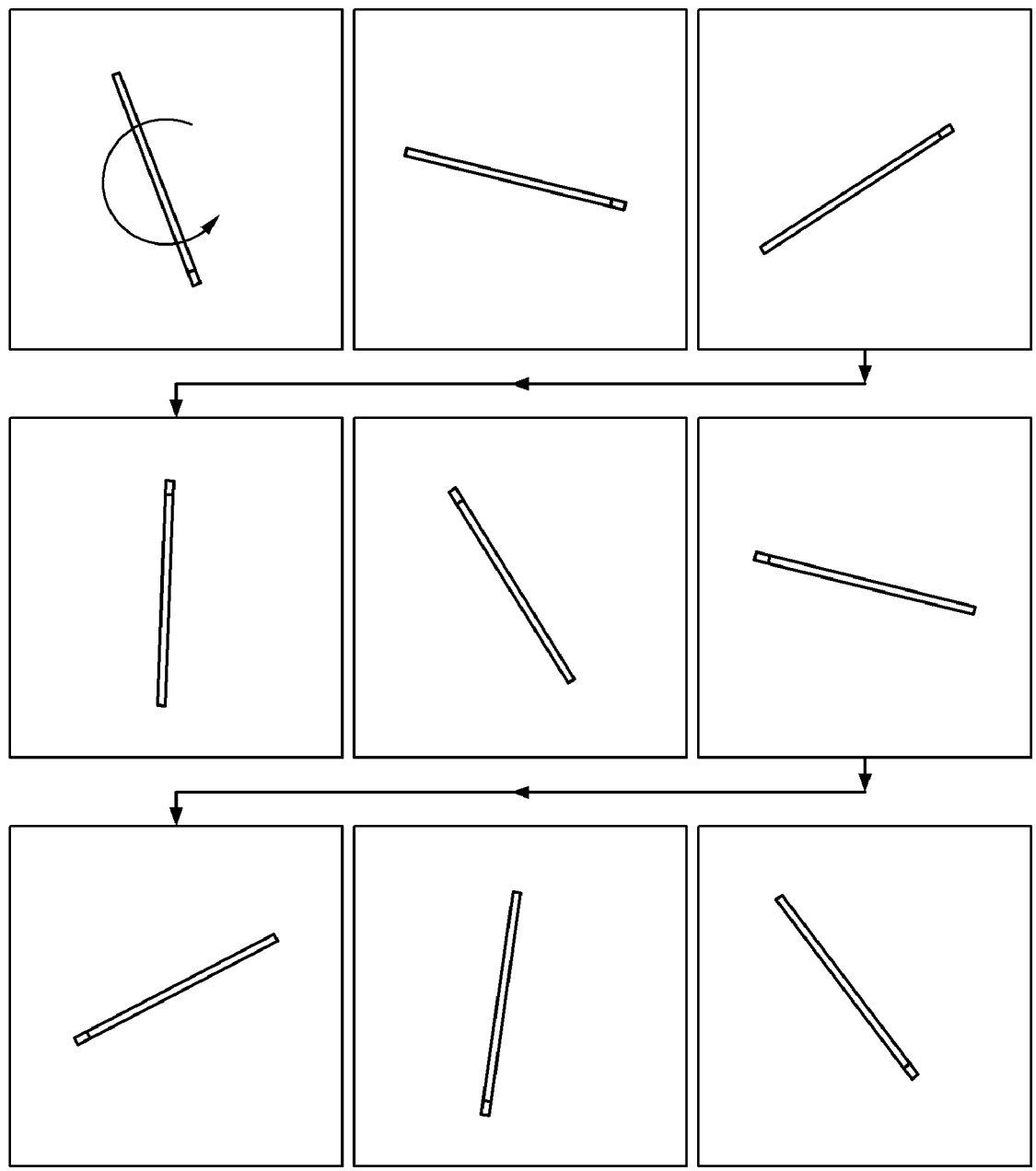
FIG. 13 is a sequence of images showing a full rotation of a 40 μm long, 1 μm diameter micro-particle.

In an exemplary method of use, the stator 82 was placed over the particle using a mechanical positioning stage 90. Micro-coils 12 of the stator 82 were individually connected to a current driver 92 having separate current amplifiers controlled by independent digital computer D/A channels. The control channels for the current driver 92 were programmed so that the electric currents through the three micro-coils 12 were sinusoidally driven at a 120 degree phase difference in respect to each other (three-phase motor), as shown in FIG. 12. This arrangement of the currents provided the sinusoidal attractive and repulsive forces to be applied to the magnetic rotor, resulting in the rotational motion of the single domain particle 86, as observed by an optical microscope 93. FIG. 13 shows a composite sequence of images demonstrating one full rotation of the single domain particle rotor 86. The peak current used in the micro-coils 12 was 100 mA, and with a coil resistance of approximately 1 Ohm, no heating problems were observed during the operation. The rotation of the motor could be reversed by simultaneously reversing the currents in any two of the stator coils. An exemplary motor was able to spin the motor at 250 rpm in a water solution inside a capillary tube, limited only by the available rate of our computer generated sinusoidal currents to the three micro-coils. Much higher rotational speeds are potentially attainable by, for example, using advanced three-phase motor controllers due to the small mass and rotational moment of inertia of the rotor, as well as the low inductance of the micro-coils and ferromagnetic micro-tips.

Figure 14:
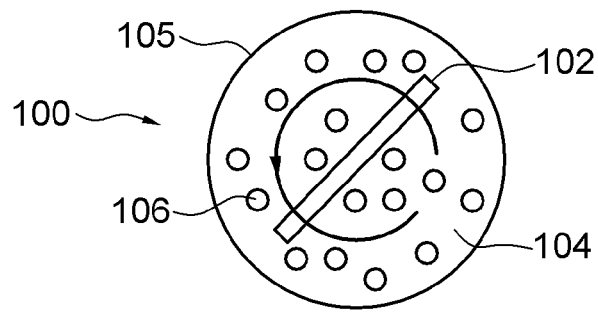
FIG. 14 is a schematic diagram of a micro-stirrer in a fluid chamber according to another embodiment of the present invention.
Figure 15:
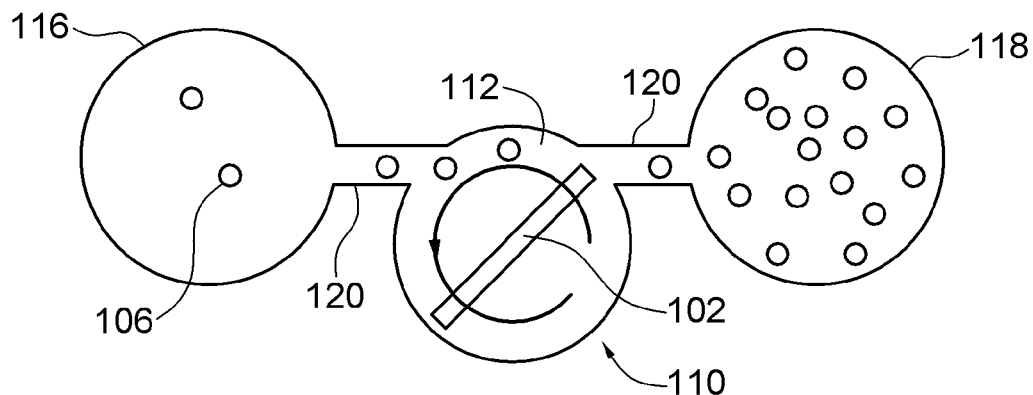
FIG. 15 is a schematic diagram of a micro-pump.
Figure 16A:
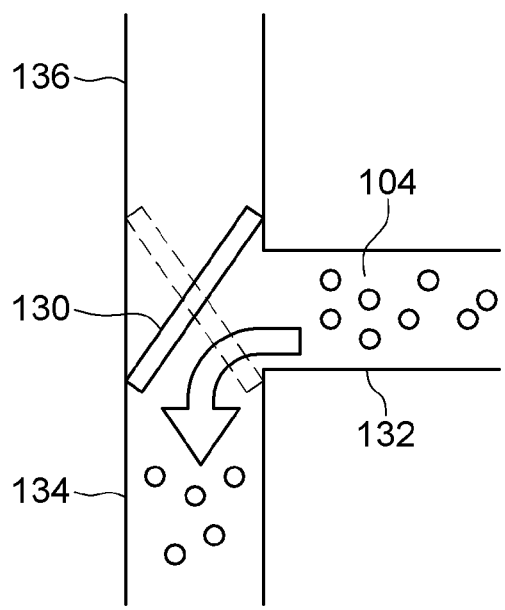
FIG. 16 is a schematic diagram of a micro-valve for fluid flow control in first and second positions for directing fluid into first and second outlet ports.
Figure 16B:
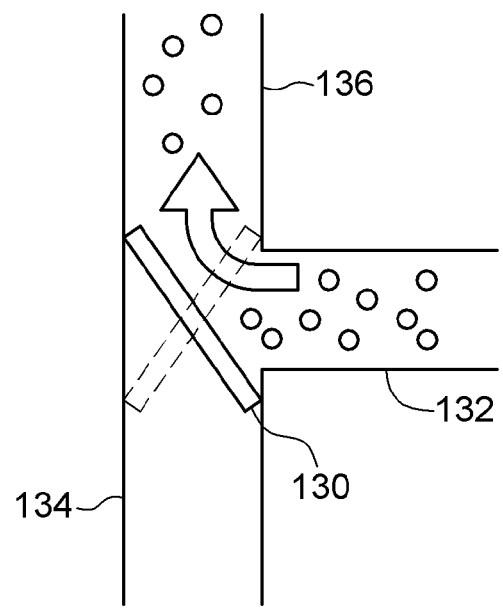

A magnetic micro-motor such as the micro-motor 80 shown and described adds potential new components to the list of available tools for "lab-on-a-chip" microfluidic systems for drug delivery, cell separation, and biomedical diagnostics. For microfluidics systems in particular, electrostatic principles that are often used for actuation can interfere with the ionic nature of the fluids. Electric isolation provided by the magnetic motors 80 of the present invention can potentially alleviate this interference problem in fluid flow control and mixing. For example, FIGS. 14-16 show exemplary components in a microfluidic system. The present invention is not intended to be limited to a particular system, however. FIG. 14 shows a micro-stirrer 100 having a rotor 102 preferably similar to the magnetic micro-particle 86 of the micro-motor 80. The micro-stirrer 100 is disposed within a fluid 104 contained in a chamber 105, which may contain one or more particles 106. A stator 82 (not shown in FIG. 14) disposed outside or inside of the fluid 104 operates to rotate the micro-stirrer 102 and manipulate the fluid.

As other exemplary embodiments of microfluidic components, a rotor may also form part of a micro-pump 110, as shown by example in FIG. 15 in a pump chamber 112 for moving the fluid 104 and particles 106 from an inlet chamber 116 to an outlet chamber 118 connected by one or more channels 120. FIG. 16 shows a rotor employed as a micro-valve 130 disposed between an inlet port 132 and first and second outlet ports 134, 136. The micro-valve can be rotated, for example, between a first position (the left diagram) for directing the fluid 104 to the first outlet port 134 and a second position (the right diagram) for directing the fluid to the second outlet port 136. It is to be understood that the components 100, 110, 130 shown in FIGS. 14-16 are exemplary, and other components for manipulating particles and fluid in a microfluidic system are contemplated by the present invention.

Figure 17:
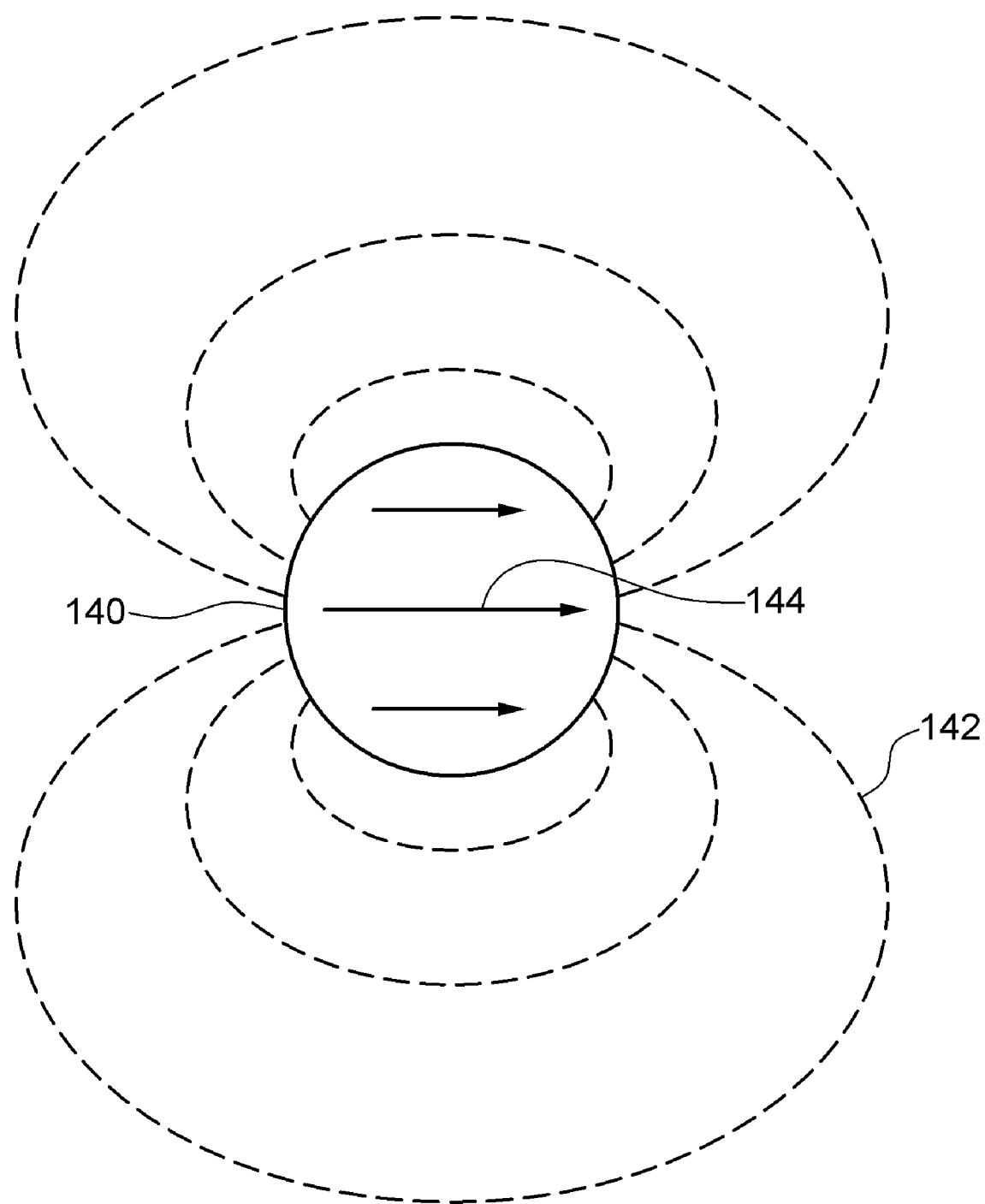
FIG. 17 is a schematic diagram of a magnetic field around a magnetic wire magnetized perpendicularly to the long axis of the wire.

Other embodiments of the present invention use magnetic wires to manipulate particles by separating one or more particles from a fluid and/or from other particles. In conventional uses of magnetic wires in MEMS applications, the magnetization of the wires is along the wire long axis. However, as shown in FIG. 17, a magnetic wire 140, for example a ferromagnetic wire can be a source of strong gradient fields 142 along the entire length of the wire if an external field is used to orient the magnetization 144 (shown as arrows) as perpendicular to the wire long axis.

According to a preferred embodiment of the present invention, this principle is used in ultra-high gradient magnetic separation applications where a fluid of interest is passed through a magnetized wire mesh. Current high gradient magnetic separation techniques use larger wire mesh sizes or larger magnetic spheres for sources of magnetic fields and field gradients. The magnetic forces depend inversely on the diameter of the magnetic wires, and therefore the smaller the wire diameter the stronger the magnetic field gradients and magnetic forces will be. Partially filled membranes with nanoscopic pores will therefore apply higher magnetic separation forces to the magnetic particles being separated from a solution. This technique also allows for chemical isolation of the ferromagnetic wires from the capillaries through which the solution moves.

Figure 18:
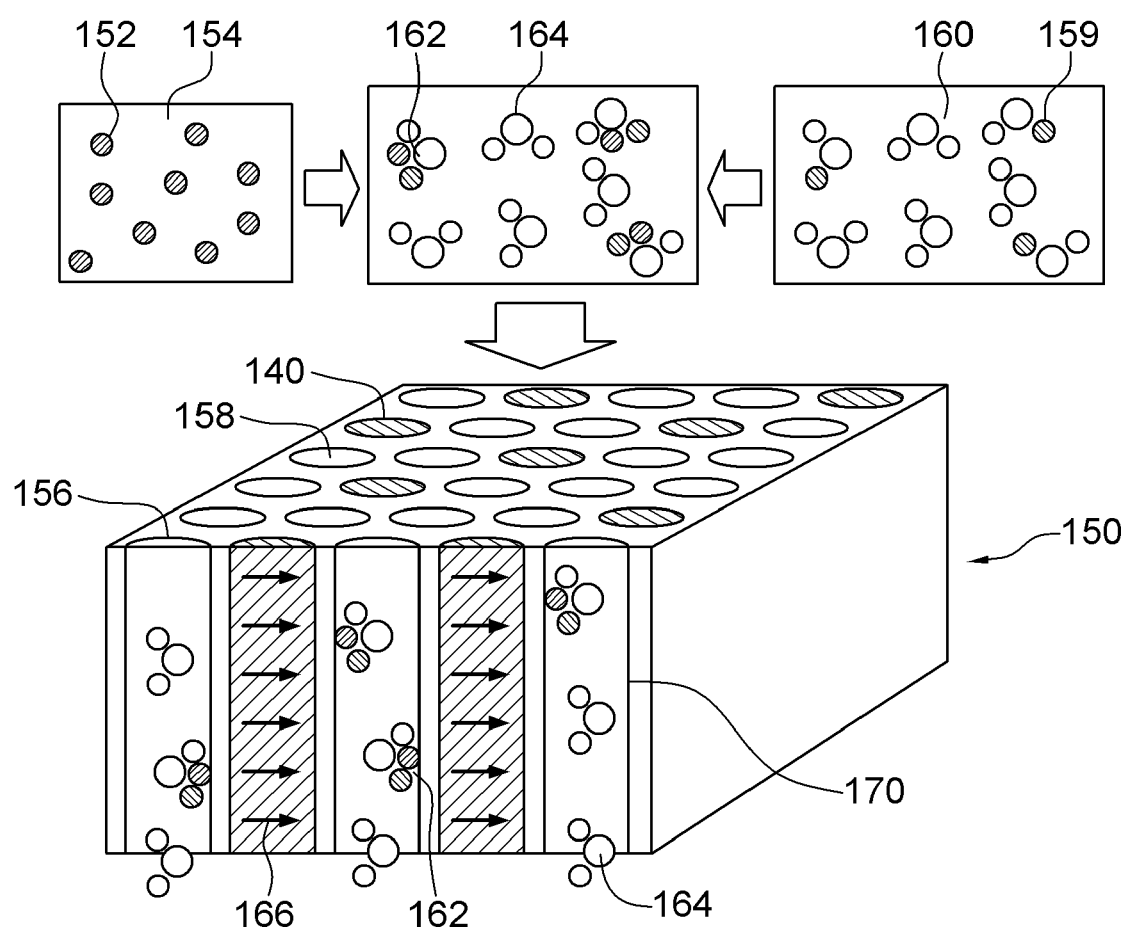
FIG. 18 is a schematic diagram showing a preferred method of operation of a high-gradient magnetic filter.

According to an embodiment of this aspect of the present invention, a nano-porous membrane 150 as shown in FIG. 18 partially filled with magnetic wires 140 provides a magnetic separation filter for magnetic separation. The magnetic separation membrane 150 allows for a higher magnetic separation force to be applied to magnetic particles 152 or beads being separated from a solution 154. In application, the membrane 150 provides efficient separation of the particles 152 from the solution 154.

Preferred embodiments of the membrane 150 allow for chemical isolation of magnetic wires from capillaries 156 through which the solution 154 moves. Furthermore, since the method embodied in this membrane 150 is based on the use of micro-channel technologies, the magnetic separation membrane and method is well-suited to be implemented into microfluidic and MEMS designs. These preferred embodiments are based on magnetic separation principles where the magnetic particle 152 or bead is attracted magnetically to the magnetized magnetic wire 140.

Preferably, the magnetic separation filter is fabricated by partially filling holes or pores 158 of the porous membrane 150 with a magnetic material by, for example, electrodeposition or melt injection to form the magnetic wires 140, for example, in a cylindrical shape. There exist various several already-established membrane systems that could be used for the porous membrane 150, and electro-deposition methods for filling the holes 158 are known by those in the art. The diameter of the pores 158 and columns can be tuned down to very small diameters (e.g., down to 1 nm), and the distance from the wires 140 to the empty pores are preferably made very small. Additionally, the membranes in the porous membrane 150 can be made very sturdy and their thickness can preferably be tuned. The empty pores 158 (where the solution 154 moves) are preferably chemically isolated from the magnetic wires 140 that provide for magnetic separation.

As shown in FIG. 18, the magnetic beads 152 on the left are preferably engineered to bind to specific sites 159 (molecules, proteins, viruses, bacteria, impurities, or other materials) and are mixed with the solution 160 on the right to form a combined solution having sites 162 with bound particles and sites 164 without bound particles. After the binding process, the combined solution is passed through the ultra-high gradient magnetic filter (the membrane 150). An external magnetic field is applied parallel to the surface of the membrane 150 in order to magnetize the magnetic wires, as shown by arrows 166. In the filter 150, the particle 162 bound to the magnetic bead 152 is trapped on the walls of capillaries 170 while the unbound units 164 are passed through. The trapped particles can later be released by removing the external magnetic field. This preferred embodiment of the present invention may used for application such as, but not limited to, the biomedical field of separation of molecules, proteins, viruses, bacteria, cells, impurities, etc, including the integration of such a system into microfluidic or MEMS systems.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. An apparatus for separation of microscopic particles from a solution, the apparatus comprising:

A nanoporous membrane comprising a plurality of pores, wherein said membrane is partially filled with magnetic wires, said magnetic wires being interspersed within the pores of said membrane, the remaining pores allowing a flow-through path for said solution; and A device for applying a magnetic field to the magnetic wires, the magnetic field being perpendicular to the long axis of said magnetic wires;

Whereby the microscopic particles are magnetically attracted to said magnetic wires when magnetized by said device for applying a magnetic field.

2. The apparatus of claim 1 wherein each of said microscopic particles comprises
at least one magnetic bead, said magnetic bead being configured to selectively bind with the microscopic particle.

3. The apparatus of claim 2 wherein the particles are of a particular system among a plurality of systems, and wherein said at least one magnetic bead is configured to bind to the particular system.

4. The apparatus of claim 1 wherein the pores have a diameter on the order of nanometers.

5. The apparatus of claim 1 wherein said pores containing magnetic wire are chemically isolated from said pores allowing a flow-through path for said solution.

6. The apparatus of claim 1 wherein said membrane comprises a wire mesh.

7. The apparatus of claim 1 wherein said magnetic wire comprises an electrodeposited or melt injected ferromagnetic material.

8. The apparatus of claim 7 wherein said magnetic wire partially fills each of said pores containing said magnetic wire.

9. The apparatus of claim 1 wherein a distance between said magnetic wires and said pores allowing a flow-through path is sufficiently small to allow said particles to be attracted to said magnetic wires.

10. The apparatus of claim 1 wherein said magnetic wire has a cylindrical shape.

11. The apparatus of claim 1 wherein the external magnetic field is applied parallel to a surface of the membrane.

12. The apparatus of claim 1 wherein said magnetic wire has an ultra-high magnetic gradient.

13. The apparatus of claim 12 wherein said magnetic wire is a source of gradient fields along the entire length of the wire.

14. A method for separating microscopic particles from a solution, the method comprising:
Binding a magnetic bead to each of the microscopic particles;
Providing a nanoporous membrane comprising a plurality of pores, wherein said membrane is partially filled with magnetic wires, said magnetic wires being interspersed within the pores of said membrane, the remaining pores allowing a flow-through path for said solution;
Applying a magnetic field external to the membrane to magnetize the magnetic wire along a direction perpendicular to the long axis of the magnetic wire; and
Passing the solution through the pores allowing a flow-through path for said solution;
Wherein the microscopic particles are attracted magnetically to the magnetized magnetic wire.

15. The method of claim 14 wherein the microscopic particles comprise magnetic beads binded to specific sites.

16. The method of claim 15 wherein the specific sites comprise at least one of molecules, proteins, viruses, bacteria, and impurities.

17. The method of claim 14 wherein said applied magnetic field is parallel to a surface of the membrane.

18. The method of claim 14 further comprising:
Partially filling the nanoporous membrane with a magnetic material to provide the magnetic wire.

19. The method of claim 18 wherein said partially filling comprises at least one of electrodepositing and melt injection.

20. The method of claim 14 wherein the magnetic wire after said applying has an ultra-high magnetic gradient.

\* \* \* \* \*

UNITED STATES PATENT AND TRADEMARK OFFICE
CERTIFICATE OF CORRECTION

| | |
|---|---|
| PATENT NO. | : 7,892,427 B2 |
| APPLICATION NO. | : 12/229975 |
| DATED | : February 22, 2011 |
| INVENTOR(S) | : Barbic et al. |

It is certified that error appears in the above-identified patent and that said Letters Patent is hereby corrected as shown below:

On the Title Page Item (56)
Under "Other Publications", left column, line 13, please delete "Mandjour et al." and insert --Mahdjour et al.-- therefor.

| | |
|---|---|
| Col. 8, line 34 | After "shown" please insert --in--. |
| Col. 10, line 13 | After "various" please delete "several". |
| Col. 10, line 39 | Please delete "may used" and insert --may be used-- therefor. |

Signed and Sealed this
Twenty-seventh Day of September, 2011

David J. Kappos
*Director of the United States Patent and Trademark Office*